(12) United States Patent
Chin (10) Patent No.: US 10,092,702 B2
(45) Date of Patent: Oct. 9, 2018

(54) SYRINGE MECHANISM FOR AUTO-REGENERATION OF DERMIS

(71) Applicants: Joong Suk Jin, Seongnam-si (KR); Se Hoon Chin, Seongnam-si (KR)

(72) Inventor: Se Hoon Chin, Seongnam-si (KR)

(73) Assignees: Joong Suk Jin, Gyeonggi-Do, Seongnam-si (KR); Se Hoon Chin, Gyeonggi-Do, Seongnam-si (KR)

(*) Notice: Subject to any disclaimer, the term of this patent is extended or adjusted under 35 U.S.C. 154(b) by 96 days.

(21) Appl. No.: 15/118,635

(22) PCT Filed: Jul. 21, 2015

(86) PCT No.: PCT/KR2015/007586
§ 371 (c)(1),
(2) Date: Aug. 12, 2016

(87) PCT Pub. No.: WO2016/036000
PCT Pub. Date: Mar. 10, 2016

(65) Prior Publication Data
US 2017/0056594 A1    Mar. 2, 2017

(30) Foreign Application Priority Data
Sep. 2, 2014  (KR) .................. 10-2014-0116046

(51) Int. Cl.
*A61M 5/31*  (2006.01)
*A61M 5/178*  (2006.01)
(Continued)

(52) U.S. Cl.
CPC .......... *A61M 5/3129* (2013.01); *A61M 5/178* (2013.01); *A61M 5/347* (2013.01);
(Continued)

(58) Field of Classification Search
CPC .... A61M 5/347; A61M 5/3129; A61M 5/178; A61M 13/003
See application file for complete search history.

(56) References Cited

U.S. PATENT DOCUMENTS 6,436,075 B1 * 8/2002 Liao .................... A61M 5/3205
604/181
8,626,270 B2 * 1/2014 Burbank ............. A61K 49/006
600/414

(Continued)

FOREIGN PATENT DOCUMENTS

| KR | 1020050067210 | 6/2005 |
|---|---|---|
| KR | 1020090023493 | 3/2009 |
| KR | 1020120013271 | 2/2012 |

OTHER PUBLICATIONS

International Search Report for international application PCT/KR2015/007586, dated Oct. 23, 2015.

*Primary Examiner* — Nathan R Price
*Assistant Examiner* — Melissa A Snyder
(74) *Attorney, Agent, or Firm* — Burris Law, PLLC (57) ABSTRACT

A syringe mechanism for the auto-regeneration of the dermis is provided. The syringe mechanism includes: a liquid syringe filled with liquid in a cylinder thereof, a piston inserted into a top of the cylinder, a discharge portion formed at a bottom portion of the cylinder, and screw threads formed around the discharge portion; and an injecting member having a cylindrical body portion, an inlet portion formed to be inserted and coupled with the discharge portion at a top end of the cylindrical body portion, and a coupling portion formed to be coupled with the screw threads around the inlet portion, the screw threads and the coupling portion rotated and inserted so as to be fastened to the liquid syringe so that liquid is injected into the top portion of the body portion via the liquid syringe.

14 Claims, 9 Drawing Sheets

(51) Int. Cl.
*A61M 5/34* (2006.01)
*A61M 5/19* (2006.01)
*A61M 5/00* (2006.01)

(52) U.S. Cl.
CPC ......... *A61M 5/19* (2013.01); *A61M 2005/006* (2013.01); *A61M 2005/1787* (2013.01); *A61M 2005/3128* (2013.01)

(56) References Cited

U.S. PATENT DOCUMENTS

2005/0074501 A1* 4/2005 Murphy ................ A61K 33/00
 424/600
2011/0011160 A1* 1/2011 Gerde ................ A61B 5/0813
 73/28.01

* cited by examiner

SYRINGE MECHANISM FOR AUTO-REGENERATION OF DERMIS

CROSS-REFERENCE TO RELATED APPLICATIONS

This application is the United States national phase of International Application No. PCT/KR2015/007586 filed Jul. 21, 2015, and claims priority to Korean Patent Application No. 10-2014-0116046 filed Sep. 2, 2014, the disclosures of which are hereby incorporated in their entirety by reference.

BACKGROUND OF THE INVENTION

Technical Field

The present invention relates to a syringe for auto-regeneration of dermis that continuously and alternately injects gas and liquid into a dermis layer of a skin by a desired amount.

Description of Related Art

In general, the dermis is a part between an outer skin and a subcutaneous tissue in the skin of the vertebrate animal, occurs from a mesoderm, and is a fiber connective tissue having a thickness of 0.3 to 2.4 mm. The dermis includes sweat glands, hair follicles, fat lines and the like, and most of the physiological functions of the skin occur here.

A characteristic symptom of the skin aging is an occurrence of wrinkles in the skin. The wrinkles occur due to a situation in which the dermis gets thinner and the elasticity is lost by the gradual regression of the extracellular matrix of the dermis, thereby bending the outer skin over the dermis. When medically explained, an amount of hyaluronic acid (HA) decreases on the dermis layer with the aging of the skin, an elongation shape of fibroblast is collapsed due to a decrease in mechanical tension caused by fragmentation of a collagen lattice network. Thus, a decrease in production of collagen and regression progress and the dermis is aged, with the result that the wrinkles occur in the upper skin.

In order to remove the wrinkles formed on the outer skin, a surgical operation for pulling and cutting the skin that has lost its elasticity, and an invasive method such as a chemical decortication for making minutely damage to the outer skin to ensure that the skin is reproduced are also used. However, the invasive method has a disadvantage of having many side effects.

Meanwhile, there are non-invasive methods such as a Botox injection method for paralyzing the muscle for a certain period of time to prevent the occurrence of wrinkles, and a method for injecting a filler to the dermis lower layer. In the case of Botox injection method, there is a disadvantage of a temporary effect (5 to 6 months). Although the Botox may prevent the wrinkles generated by the folded skin due to the movement of muscle by preventing the movement of the muscle, there are limitations that cannot solve the wrinkles that have already occurred even when the skin loses the elasticity and there is no contraction of muscle. Because it is practically impossible to correctly inject a uniform amount of filler into the dermis layer just below the wrinkles, and an uneven irregular surface is made, it is hard to perform the method of injecting the filler into the dermis layer. Further, because the filler is also absorbed after six to nine months, there is a disadvantage of a temporary effect.

Korean Patent Application No. 10-2012-0013271 A entitled "syringe for auto-regeneration of dermis and treatment method" is the applicant of the inventors of the present invention that discloses a syringe that injects a gas such as carbon dioxide into the dermis layer of the wrinkled skin to apply a minute separation damage to the site of the dermis layer, while the gas is widely diffused to the site, and injects a liquid such as hyaluronic acid or collagen solution diluted with water into the separation space formed accordingly.

When alternately injecting the gas and liquid into the dermis layer or the dermis lower layer of the skin in this way, the blood flow of the capillary of the dermis layer increases, the active switching of the collagenous tissue is induced, new collagen is produced on the dermis layer of the wide site, and the dense arrangement of fibers is formed. Thus, wrinkles of the upper outer skin are lost or get thinner. This method has no side effect, and has an advantage that the effect of the wrinkle removal is maintained for a long period of time.

Furthermore, as a result of the previous researches, it was checked that this treatment method has an excellent effect capable of easily curing the depression wounds of various forms such as laceration sink scar, chickenpox scar, pimple scar and nail mark which could not be solved by any existing surgical techniques such as fractional laser, decortication, chemical peeling and scar removal as well as wrinkle care.

Accordingly, even when the gas is injected into the syringe filed with liquid at the time of the initial production through the check valve, the liquid is always present in the dead space from the bottom of the check valve to the syringe needle. Accordingly, at the beginning of pushing of the piston after the invasion, there was a problem in which some liquid is injected rather than the gas being injected into the dermis, thereby failing to perform a perfect treatment effect.

Furthermore, because the liquid for treatment is typically circulated while being contained in a liquid syringe, in order to cause the liquid to pass through the dermis, a stopper coupled to the discharge portion is removed, and the injection needle is used by being directly fitted to the discharge portion. Thus, in the case of treatment that needs to alternately inject gas and liquid, there was a troublesome for use. Therefore, in the prior invention, in order to overcome such a troublesome, the liquid is used, while being contained in a syringe that can simultaneously invade the gas and the liquid. At this time, because the liquid contained in the liquid syringe is relatively expensive, there was a disadvantage that it is necessary to mold the liquid syringe by an expensive material in order to prevent the alteration or loss of the liquid.

Further, because the liquid is used, while being contained in the syringe provided with the check valve, the site of treatment is small. Thus, even when the liquid remains, it is difficult to recover or reuse the remaining liquid, the remaining liquid is discarded as it is, and the user bears the expense. Thus, there was a disadvantage of high treatment cost. Further, because there is no additional method for adjustment of the amount discharged through the needle of the syringe to which the method is during the treatment, there was a problem of difficulty in minute adjustment of an amount of contents discharged during treatment.

Thus, there was an urgent need for a syringe mechanism for auto-regeneration of dermis that can perform treatment without leaving a relatively expensive liquid, by suppressing a dead space to a minimum, while directly using a liquid syringe distributed in a state of normally containing the liquid, and can recover and reuse the liquid when remaining.

Matters described as the background art are merely intended to facilitate the understanding of the background of the present invention, and should not be recognized as corresponding to the prior art that has been already known to those skilled in the art.

SUMMARY OF THE INVENTION

An aspect of the present invention provides a syringe mechanism for auto-regeneration of dermis that can alternately use gas and liquid by a single syringe even when used by being directly connected to a generally distributed syringe containing the liquid, can recover and reuse the liquid when the relatively expensive liquid remains after treatment, and can finely adjust an amount of liquid discharged to a needle through a body of an injecting member to enhance an accuracy of treatment.

According to an aspect of the present invention, there is provided a syringe mechanism for auto-regeneration of dermis that includes: a liquid syringe in which a liquid is filled inside a cylinder, a piston is inserted into an top of the cylinder, a discharge portion is formed at a bottom portion of the cylinder, and screw threads are formed around the discharge portion; and an injecting member in which a cylindrical body portion is provided, an inlet portion is formed to be inserted and coupled with the discharge portion at the top of the body portion, a coupling portion is formed to be coupled with the screw threads around the inlet portion, the screw threads and the coupling portion are rotated and fitted so as to be fastened to the liquid syringe so that liquid is injected into the top portion of the body portion via the liquid syringe, an inlet check valve is provided at one side of the bottom portion so that gas is injected into the bottom portion via the inlet check valve, and a needle is coupled to the bottom so that gas or liquid from the body portion is discharged to the outside.

The inner diameter of the body portion may be 2 to 7 mm.

An inner surface of the body portion may have an inner diameter that becomes increasingly narrower as it goes toward the lower side.

The inner surface of the body portion may be an inverted cone-shape.

A top corner of the inner side surface of the body portion may be a round shape.

A bottom edge of the inner side surface of the body portion may be a round shape.

The top of the needle may be located between a point which is 2 mm below the bottom of the inlet check valve and a point which is 5 mm above the top of the inlet check valve.

The syringe mechanism may further include a gas supply portion connected to the inlet check valve.

A double tube which opens downward is formed on the lower surface of the cylinder, the inner tube of the double tube communicates with the cylinder to constitute the discharge portion, a screw thread is formed on an inner circumferential surface of an outer tube of the double tube, and a coupling portion of the injecting member has a flange shape formed along the periphery of the inlet portion, is inserted between the inner tube and the outer tube of the double tube and can be coupled to the screw thread.

The discharge portion may be inserted into the inner diameter of the inlet portion in accordance with the screw coupling of the coupling portion and the screw thread.

Further, the discharge portion has a cone-shape having an outer diameter that becomes narrower as it goes downward, and the discharge portion may be sealed in close contact with the inlet portion in a state of being inserted into the inlet portion.

The inlet portion is an open hole formed at the top of the body portion of the injecting member, and the coupling portion may be a flange shape formed along the periphery of the body portion of the point in which the open hole is formed.

The discharge portion which communicates with the cylinder and opens downward is formed on the lower surface of the cylinder, the screw thread is formed on the outer circumferential surface of the discharge portion, the coupling portion of the injecting member is the screw thread formed along the inner circumferential surface of the inlet portion, and the discharge portion may be inserted and screwed into the inlet portion.

A double tube which opens downward is formed on the lower surface of the cylinder, the inner tube of the double tube communicates with the cylinder to constitute the discharge portion, the outer tube of the double tube has a screw thread formed on its outer circumferential surface, a double tube that opens upward is formed on the upper surface of the body portion, the inner tube of the double tube communicates with the body portion to constitute the inlet portion, the coupling portion of the injecting member is the screw thread formed on the inner circumferential surface of the outer tube, and the outer tube of the cylinder is inserted between the inner and outer tubes of the body portion such that the screw threads can be coupled to each other.

According to the syringe mechanism for auto-regeneration of dermis having the aforementioned structure, by using the injecting member of the present invention formed separately by being coupled to the conventional liquid syringe circulated on the market, it is possible to differently manufacture the material of the injecting member and the material of the relatively expensive the liquid syringe, and the costs are reduced. Since the injecting member is separately molded, the injecting member is easily molded, and there is an advantage capable of repeatedly reusing the injecting member.

In the case of the body portion, when the viscosity of the liquid used during treatment is low, a cylindrical body portion may be used. However, when the viscosity of the liquid is high, when the cylindrical body portion is used, a dead space is present on the upper and lower corner sides, and a cushion effect due to the residual gas remaining in the dead space occurs. Thus, there an effect of removing the dead space to prevent the cushion effect, by forming the upper or lower corner side of the body portion in a round shape.

Further, there is an advantage that is capable of finely adjusting the amount of gas or liquid discharged through the needle of the injecting member by limiting the shape of the body portion side to an inverted cone shape, thereby enhancing the accuracy of treatment.

Further, the dead space between the bottom of the cylinder and the check valve is suppressed to a minimum by limiting the internal diameter of the injecting member and the needle position, thereby preventing the discharge of liquid during the initial pressurization of the piston such that only the gas can be injected to the dermis. As a result, it is possible to completely perform injection in the order of gas-liquid-gas to the inside of the dermis. Further, by reducing the dead space, the liquid remaining in the cylinder can be fully used in the final step of finally using all the liquid, and the residual liquid can be easily recovered only by a simply operation when the liquid remains. Accordingly, there are advantages capable of efficiently using the relatively expensive liquid and preventing a cushioning effect.

DESCRIPTION OF THE INVENTION

Hereinafter, embodiments of the invention will be described in detail with reference to the accompanying drawings. The drawings are attached hereto to help explain exemplary embodiments of the invention, and the present invention is not limited to the drawings and embodiments. In the drawings, some elements may be exaggerated, reduced in size, or omitted for clarity or conciseness.

Figure 3:
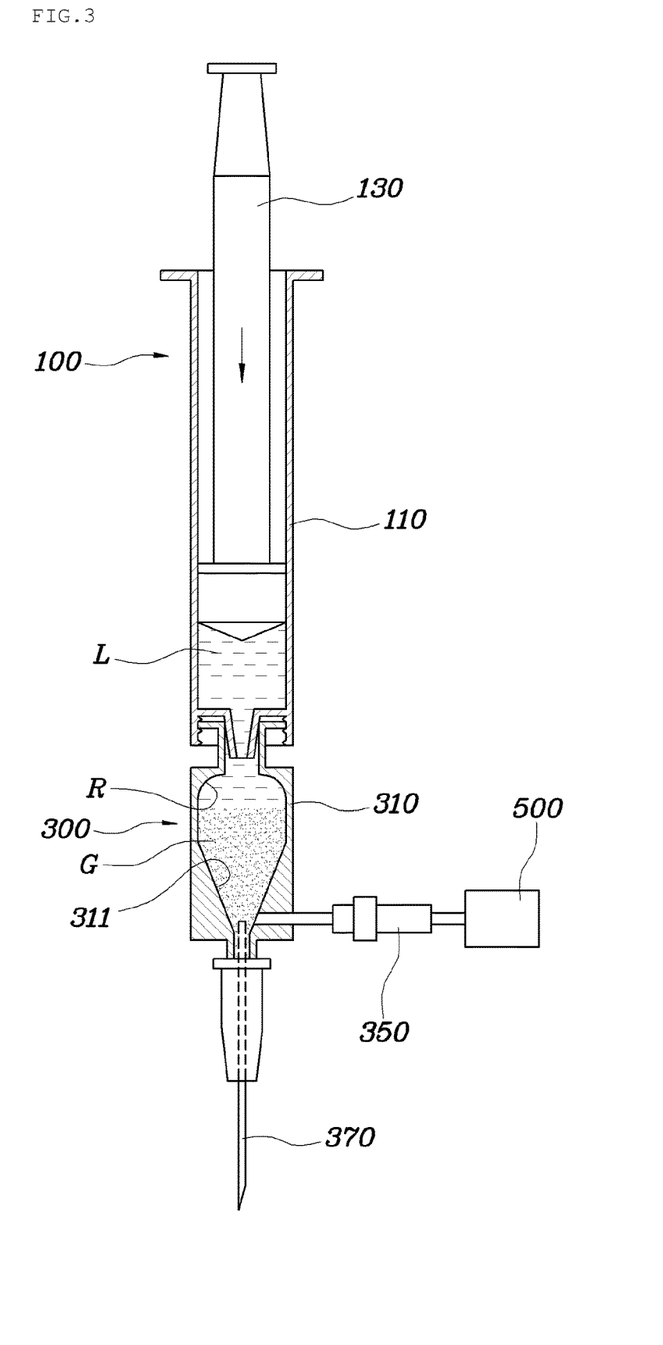
Figure 4:
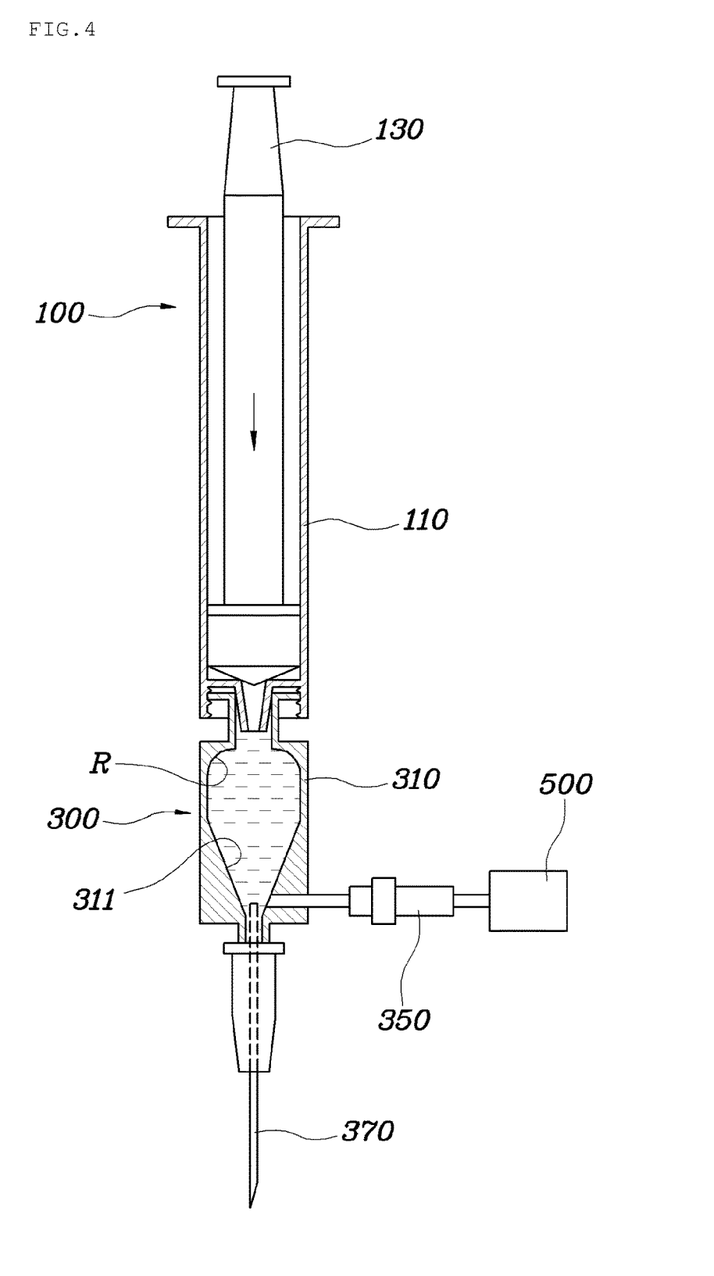
Figure 5:
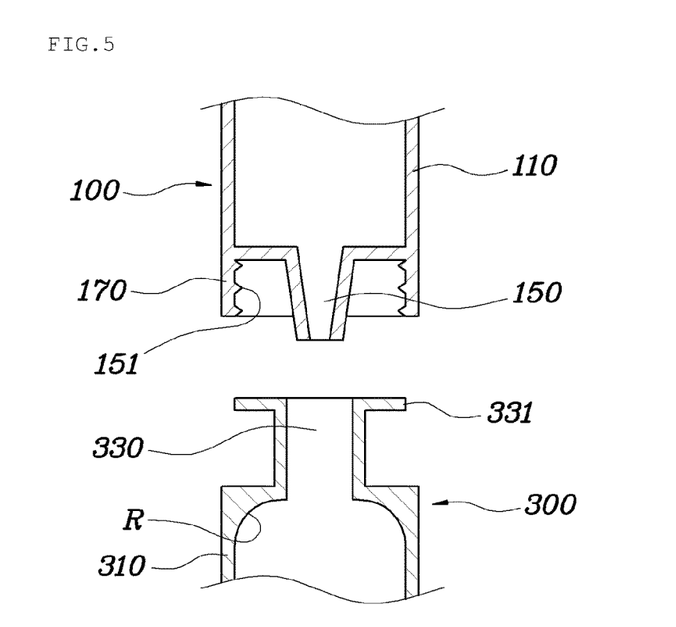
FIGS. 5 to 7 are enlarged views of a part A of FIG. 1.
Figure 6:
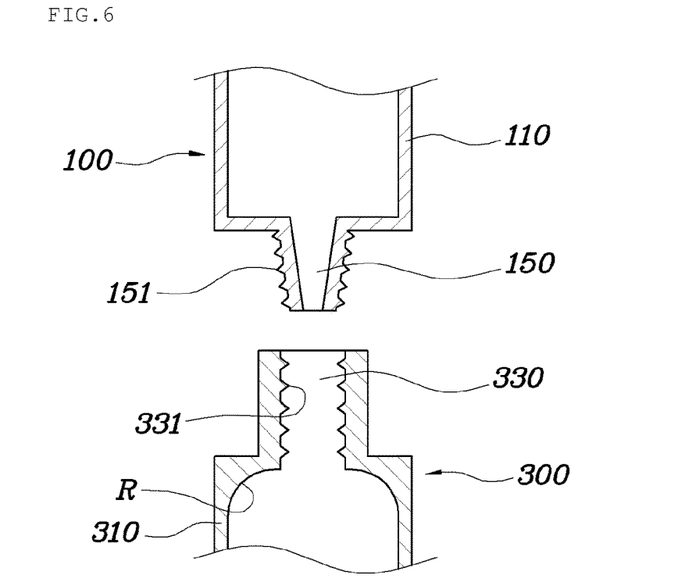
Figure 7:
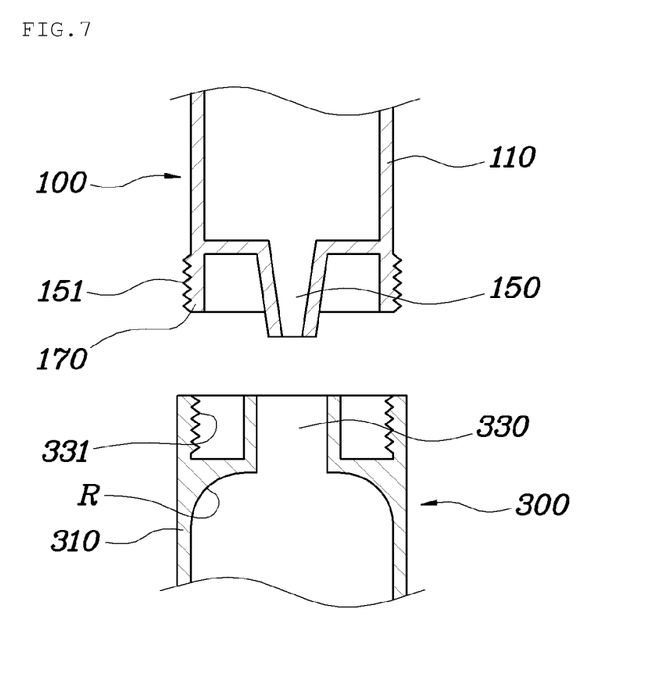
Figure 8:
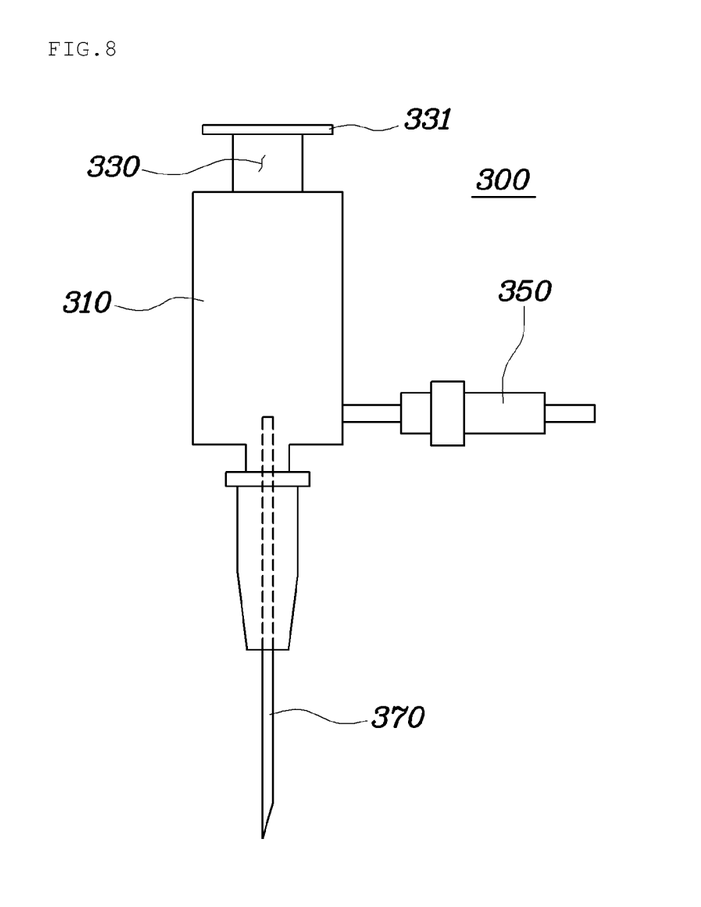
FIG. 8 is a diagram illustrating an injecting member.
Figure 9:
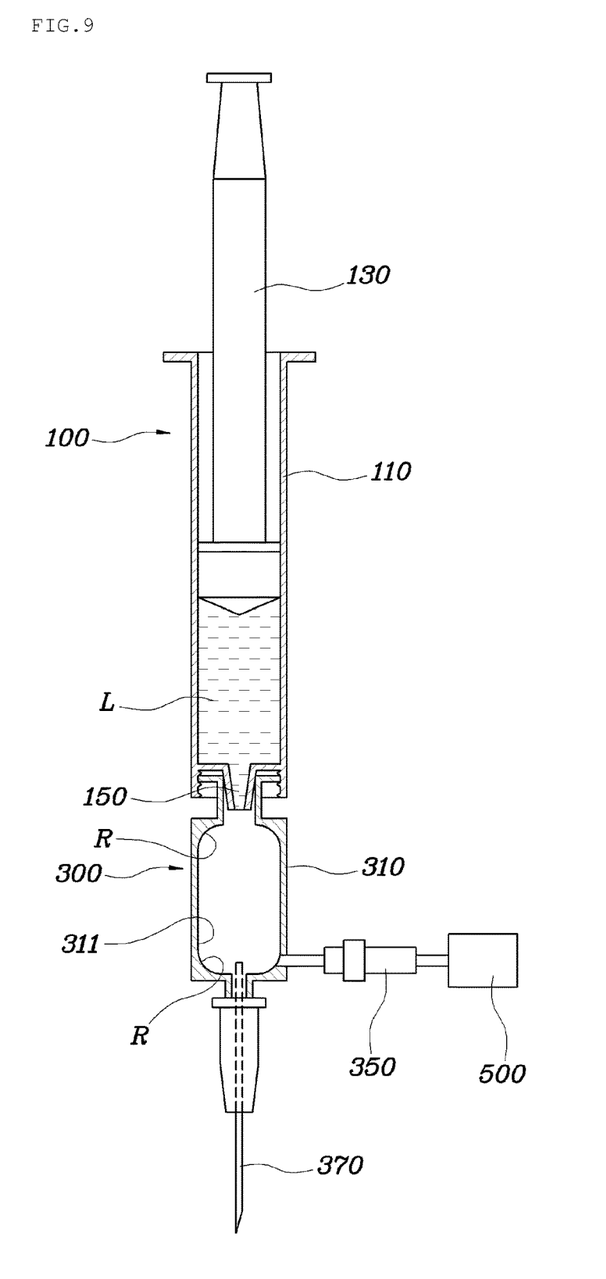
FIGS. 9 through 10 are diagrams illustrating a syringe mechanism for auto-regeneration of dermis according to two other embodiments of the present invention.
Figure 10:
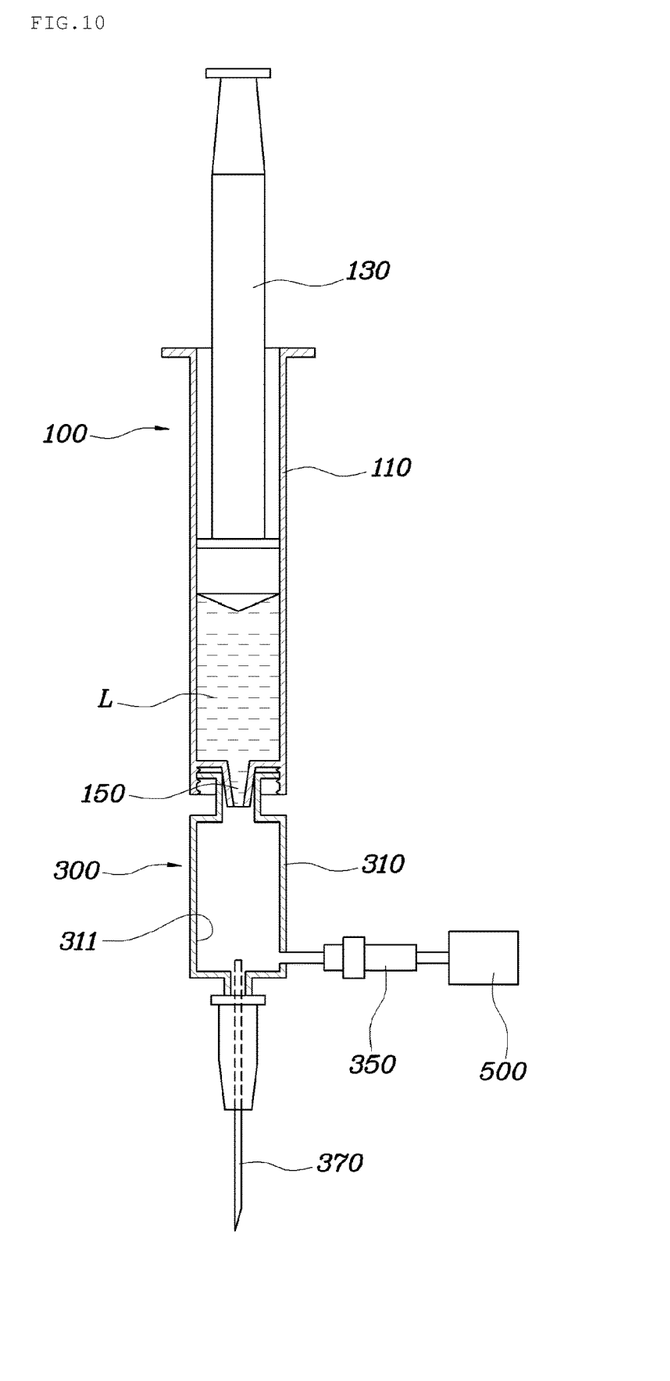

FIGS. 1 through 4 are diagrams illustrating a syringe mechanism for auto-regeneration of dermis according to an embodiment of the present invention. FIGS. 5 to 7 are enlarged views of a part A of FIG. 1. FIG. 8 is a diagram illustrating an injecting member. FIGS. 9 through 10 are diagrams illustrating a syringe mechanism for auto-regeneration of dermis according to two other embodiments of the present invention.

A syringe mechanism for auto-regeneration of dermis according to the present invention includes a liquid syringe 100 in which a liquid L is filled inside a cylinder 110, a piston 130 is inserted into an top of the cylinder 110, a discharge portion 150 is formed at a bottom of the cylinder 110, and screw threads 151 are formed around the discharge portion 150; and an injecting member 300 in which a cylindrical body portion 310 is provided, an inlet portion 330 is formed to be inserted and coupled with the discharge portion 310 at the top of the body portion 310, a coupling portion 331 is formed to be coupled with the screw threads 151 around the inlet portion 330, the screw threads 151 and the coupling portion 331 are rotated and fitted so as to be fastened to the liquid syringe 100 so that liquid is injected into the top portion of the body portion 310 via the liquid syringe 100, an inlet check valve 350 is provided at one side of the bottom portion so that gas is injected into the bottom portion via the inlet check valve 350, and a needle 370 is coupled to the bottom so that gas G or liquid L of the body portion 310 is discharged to the outside.

The liquid injector 100 of the present invention may be a syringe for dermis regeneration playback which is generally circulated by containing the liquid L therein on the market. The liquid syringe 100 includes a cylinder 100, and a piston 130 located therein. However, the injecting member 300 includes a body portion 310, an inlet portion 330 formed at the top of the body portion 310, and an inlet check valve 350 and a needle 370 provided at the bottom of the body portion 310. The injecting member 300 is interconnected with the liquid injector 100 via the coupling portion 331 such that the liquid L is injected into the upper portion of the body portion 310 through the liquid syringe 100, the gas G is injected into the bottom portion through the inlet check valve 350 such that, after the lower gas G is first injected into the dermis when pressing the piston 130, the liquid L can be injected. The gas G is injected again through the inlet check valve 350 if necessary such that the liquid L can be injected after injection of the gas G. Thus, it is possible to alternately inject the liquid L and the gas G and perform the treatment on the dermis, only by coupling the injecting member 300 to the liquid syringe 100, even if a syringe for using the liquid L and a syringe for using the gas G are not used separately.

Figure 1:
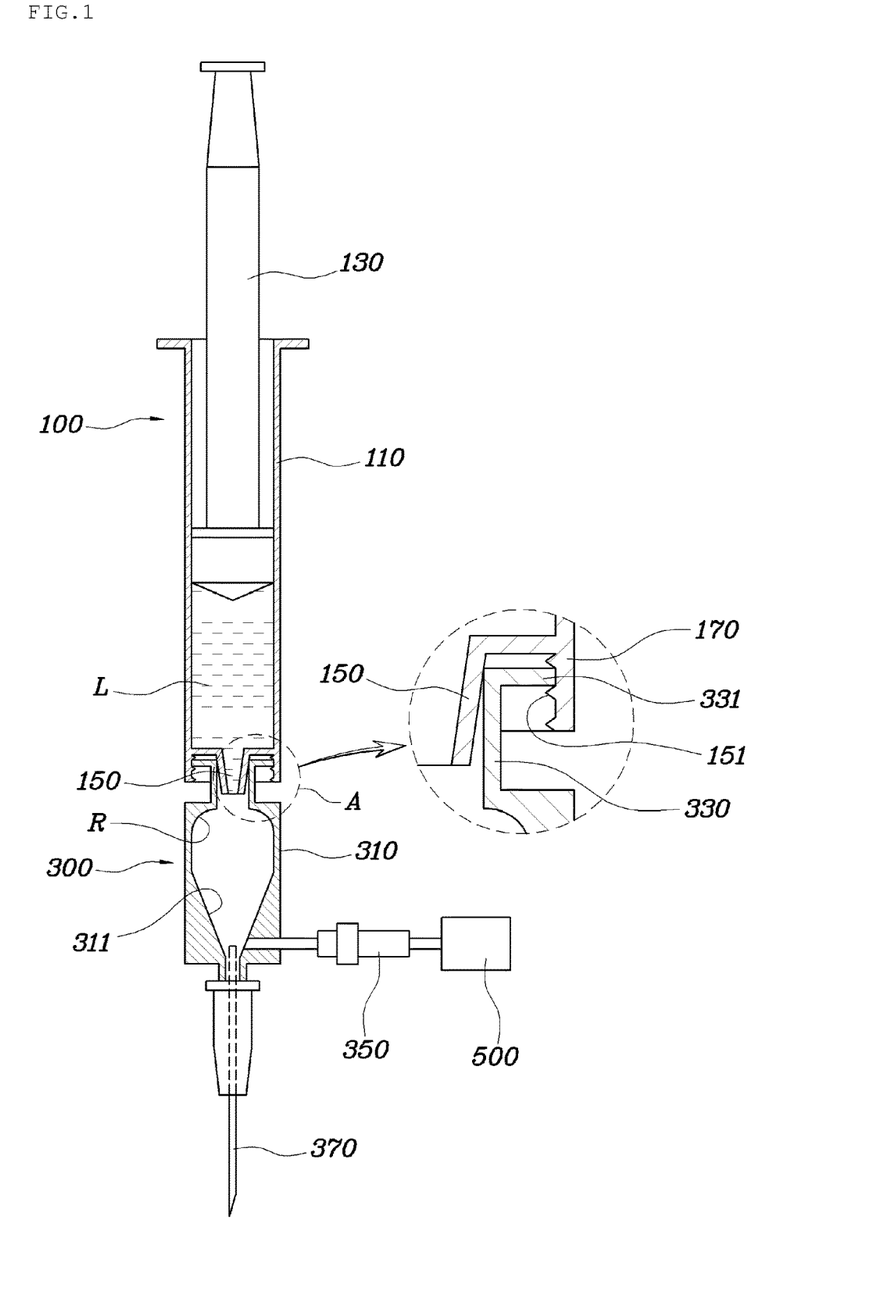
FIGS. 1 through 4 are diagrams illustrating a syringe mechanism for auto-regeneration of dermis according to an embodiment of the present invention.

Specifically, in the case of the injecting member body portion 310 of the present invention as illustrated in FIG. 1, since it is necessary to use the surface tension and the viscosity of the liquid L to be filled therein, the injecting member body portion is formed by a thin tube having an inner diameter of 2 to 7 mm. Therefore, since the inner diameter of the body portion 310 is limited to 2 to 7 mm, at the time of injection of the gas G through the inlet check valve 350, even when the gas G is injected by the surface tension and the internal viscosity of the filled liquid L, the liquid L is fully pushed upward, the liquid L is placed at the top, the gas G is located at the bottom, and the top of the needle 370 is located just after the gas. Therefore, because only the gas G is injected and the liquid L is not injected at an initial stage when only the gas G needs to be injected during treatment, it is possible to further enhance the effect of treatment. Furthermore, even if the relatively expensive liquid L remains after treatment, the residual liquid L can be easily recovered by only a simple operation without contamination.

Further, as illustrated in FIGS. 9 and 10, the injecting member body portion 310 may also be formed in a cylindrical shape, the inner surface top corner of the body portion 310 may have a round (R) shape, and the inner surface bottom corner of the body portion 310 may have a round (R) shape. When the viscosity of the liquid L to be used is low, it is possible to sufficiently perform the treatment even by in the syringe mechanism of FIG. 10. However, when the viscosity of the liquid L to be used is high, a dead space is generated on the top or bottom corner sides of the injecting member body portion 310 by the viscosity of the liquid L at the time of alternately injecting the liquid L and the gas G when the liquid L to be used is high. When the residual gas G remains in the dead space, the cushion effect is generated in which the internal pressure of the body portion 300 increases by the residual gas G at the time of injection of the liquid L, and it is difficult to perform the precise and regular treatment of the liquid L on the dermis during treatment. Therefore, by forming the top or bottom corners of the body portion 310 in a round shape as illustrated in FIG. 9, even when alternately injecting the gas G and the liquid L at the time of using the liquid L of high viscosity, a dead space is not formed to prevent the cushion effect preventing, the gas G and the liquid L can be precisely injected, and there is an effect of an increases in accuracy of treatment.

The inner surface of the injecting member body portion 310 is formed so that its inner diameter becomes increasingly narrower as it goes toward the lower side. In particular, the inner surface of the body portion 310 may have an inverted cone shape. Since the inner diameter of the body portion 310 becomes increasingly narrower as it goes toward the lower side, even when the piston 130 moves through the same stroke, the volume of the liquid L discharged through the discharge portion 150 gradually decreases. Therefore, unlike when the body portion 310 is formed in a cylindrical shape, the volume of liquid L to be discharged decreases, and it is possible to more finely adjust the amount of liquid L and gas G to be injected into the dermis, thereby more evenly charging the liquid and the gas into the dermis.

Figure 2:
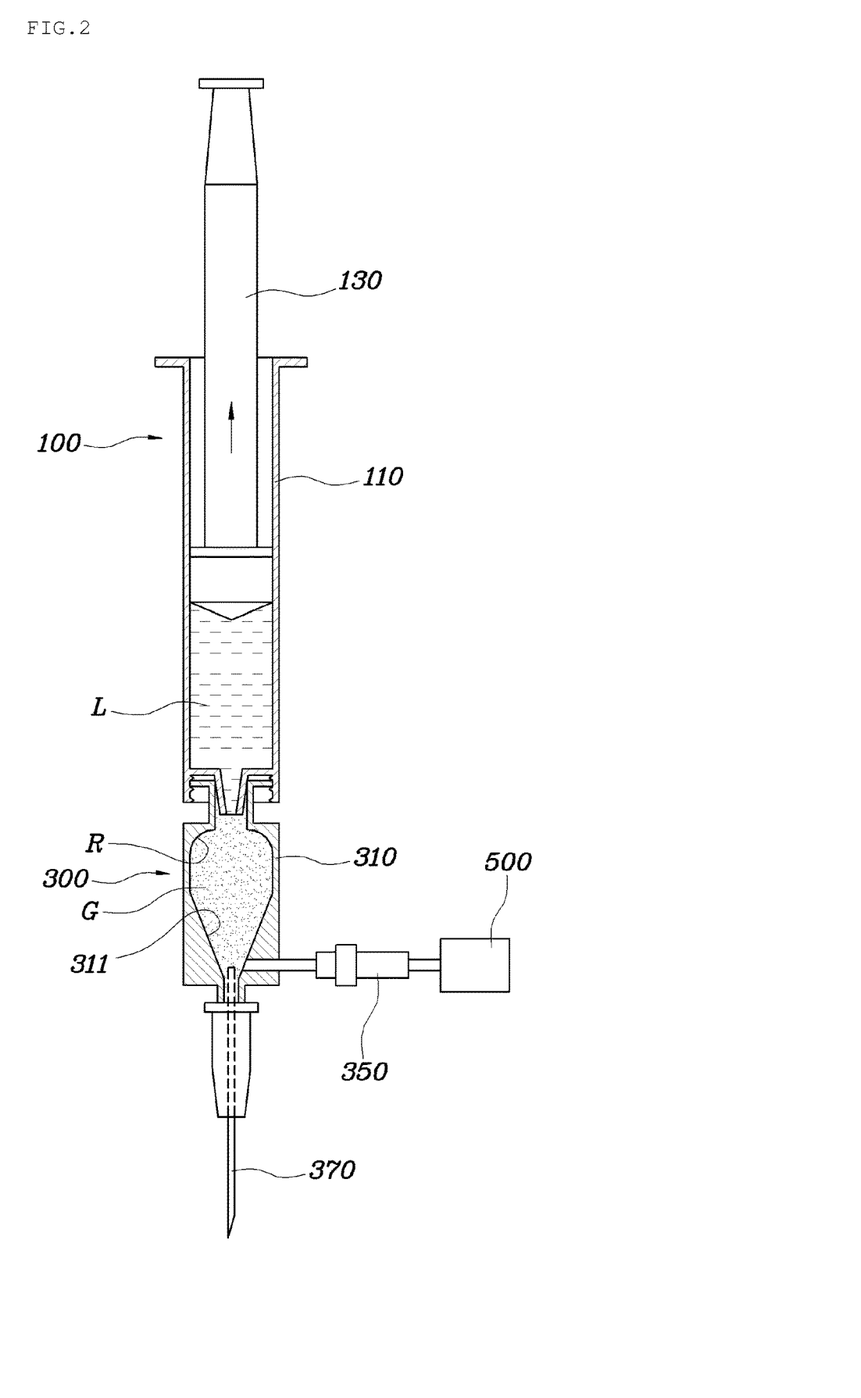

An inlet check valve 350 is provided on one side of the bottom portion of the body portion 310, and a gas supply portion 500 capable of supplying the gas G from the exterior to the interior is connected to the inlet check valve 350, such that the gas G is filled in the body portion 310 from the gas supply portion 500 via the inlet check valve 350. The gas supply portion 500 is capable of maintaining a constant pressure above an atmospheric pressure, such that the gas G is filled in the interior of the body portion 310 as illustrated in FIG. 2 through the inlet check valve 350 according to the volume that is pulled when a user pulls the piston 130. In the case of the inlet check valve 350, because it has characteristics of allowing the fluid to pass only to one side, the fluid does not pass to the exterior from the interior of the body portion 310. However, the inlet check valve 350 allows the gas to pass to the interior from the exterior of the body portion 310 through the inlet check valve 350. Thus, the gas G is filled in the body portion 310 through the inlet check valve 350, and is discharged to the dermis through the needle 370.

FIG. 1 illustrates a state in which the liquid L is initially filled in the cylinder 110. In the case of liquid L, by being filled with hyaluronic acid or collagen aqueous solution diluted with water is filled, the liquid is injected into the space of the dermis filled with the gas G. In this case, only the treatment liquid L is filled in the space formed between the bottom of the cylinder 110 and the piston 130 through a manufacturing process.

Thereafter, the gas G is filled in the injecting member 300 through the inlet check valve 350 as illustrated in FIG. 2. Accordingly, after the liquid syringe 100 and the injecting member 300 are coupled to each other, the user lowers the piston 130 by a predetermined distance so that the liquid L is lowered up to the injecting member 300, and then after pulling the piston 130 again for injection of the gas G, the gas G is filled.

Here, the top of the needle 370 is preferably provided to correspond to a point on which the inlet check valve 350 is located. The reason is that, because only the gas G rather than the liquid L needs to be preferentially injected into the dermis at the time of start of treatment, when limiting the top of the needle 370 in this way, the gas G is filled from the top of the needle 370, and when initially pressing the piston 130, the gas G is preferentially discharged through the needle 370 accordingly. Therefore, the needle 370 is limited so that its top is located between a point below 2 mm of the bottom of the inlet check valve 350 and a point above 5 mm of the top of the inlet check valve 350.

The reason is that, when the top of the needle is located below to exceed 2 mm from the bottom of the inlet check valve 350, there is a problem in which the liquid L rather than the gas G is first injected by a dead space at the time of the first injection, and when the top of the need is located above to exceed 5 mm from the top of the inlet check valve 350, there is a problem of excessive remaining of the residual gas in the space between the top of the needle 370 and the inlet check valve 350, and thus, after the gas G is compressed above a certain level, because the remaining gas G performs the role of a cushion due to the inertial pressure of the remaining gas G, there is a problem of difficulty in precisely controlling the injection amount of the liquid. Therefore, by limiting the position as described above, it is desirable to discharge only the gas G at the time of initial injection and to completely discharge the liquid L at the final injection.

In this state, when pressing the piston 130 as illustrated in FIG. 3, the gas G is first injected via the needle 370. The regeneration of dermis is treated by repeating the following process. That is, after the gas G is completely injected, some of the liquid L is injected. After the invasion of the needle to other parts of the skin, the gas G is filled again as illustrated in FIG. 2. Thereafter, the filled gas G is put into the dermis as illustrated in FIG. 3, and the liquid L is injected again as illustrated in FIG. 4. That is, the process of the gas G filling-the gas G injection-the liquid L injection-the gas G filling-the gas G injection-the liquid L injection is repeatedly performed.

Even when almost all of the liquid L is exhausted in the final step of such a treatment, the process of finally injecting the liquid L as illustrated in FIG. 4 is performed. Further, in this case, because the body portion 310 is formed between the bottom dead center of the cylinder 110 and the top of the needle 370, the piston 130 is properly used to completely inject the liquid L remaining in the body portion 310 into the skin, and the treatment can be finished.

The liquid L to be injected is hyaluronic acid or collagen aqueous solution diluted with water. However, because its cost is considerably expensive, some patients may feel burden. Thus, there is an advantage that the treatment price becomes cheaper, by completely using up the liquid L.

Further, as illustrated in FIGS. 5 through 7, the liquid syringe 100 and the injecting member 300 are formed as separate members and are coupled to each other. Therefore, because the injecting member 300 of the present invention can be used by being coupled to the conventional liquid syringe 100 containing the liquid distributed in the market, the injecting member 300 can be made of relatively inexpensive another material, unlike the liquid syringe 100 that is easily used and needs to be made of an expensive material, and there is an effect that the cost is reduced.

First, considering the coupling between the liquid syringe 100 and the injecting member 300 illustrated in FIG. 5 according to an embodiment of the present invention, a double tube 170 which opens downward is formed on the lower surface of the cylinder 110, the inner tube of the double tube 170 communicates with the cylinder 110 to constitute the discharge portion 150, and a screw thread 151 is formed on an inner circumferential surface of an outer tube of the double tube 170. A coupling portion 331 of the injecting member 30 has a flange shape formed along the periphery of the inlet portion 330 and is inserted between the inner tube and the outer tube of the double tube 170, thereby being coupled with the screw thread 151. At this time, the discharge portion 150 is inserted into the inner diameter of the inlet portion 330 in accordance with the screw coupling between the coupling portion 331 and the screw thread 151, and the liquid in the cylinder 110 is injected to the top of the injecting member body portion 310 through the discharge portion 150.

Further, the discharge portion 150 has a cone-shape having an outer diameter that becomes narrower as it goes downward, and the inner diameter of the inlet portion 330 is formed to be smaller than the outer diameter of the top of the discharge portion 150 by a predetermined size. Accordingly, at the time of coupling between the discharge portion 150 and the inlet portion 330, unlike the same inner diameter of the inlet portion 330, the outer diameter of the discharge portion 150 gradually increases as it goes toward the upper side. Accordingly, the discharge portion 150 is increasingly tightened while being inserted into the inlet portion 330, so that the inner diameter of the inlet portion 330 comes into tightly close contact with the outer diameter of the discharge portion 150. Therefore, even if a separate sealing member is not used, the effect of sealing occurs, which prevents the liquid in the liquid syringe 100 from flowing out to the outside even when pressing the piston 130, thereby preventing the waste of the relatively expensive liquid.

The inlet portion 300 is an open hole formed at the top of the body portion 310 of the injecting member 300, and the coupling portion 331 is formed in a flange shape formed along the periphery of the body portion 310 of the point in which the open hole is formed. Thus, the liquid syringe 100 and the injecting member 300 are mutually coupled to each other by screwing the discharge portion 150 and the coupling portion 331. Further, the discharge portion 150 is formed longer than the length of the outer tube of the discharge portion 170 by a predetermined length, thereby guiding the insertion of the discharge portion 150 into the inlet portion 330 when coupled with the inlet portion 330 of the body portion 310 to serve to facilitate the fastening between the liquid syringe 100 and the injecting member 300.

FIG. 6 is a diagram illustrating the coupling between the liquid injector 100 and the injecting member 300 according to another embodiment of the present invention. On a lower surface of the cylinder 110, the discharge portion 150 which communicates with the cylinder 110 and opens downward is formed. A screw thread 151 is formed on the outer circumferential surface of the discharge portion 150, and the coupling portion 331 of the injecting member 300 is a screw thread 151 formed along the inner circumferential surface of the inlet portion 330, and the discharge unit 150 is inserted and screwed into the inlet portion 330.

FIG. 7 is a diagram illustrating the coupling between the liquid injector 100 and the injecting member 300 according to still another embodiment of the present invention, a double tube 170 which opens downward is formed on the lower surface of the cylinder 110, and the inner tube of the double tube 170 communicates with the cylinder 110 to constitute the discharge portion 150. A screw thread 151 is formed on the outer circumferential surface of the outer tube of the double tube 170, and a double tube which opens upward is formed on the upper surface of the body portion 310. The inner tube of the double tube communicates with the body portion 310 to constitute an inlet portion 330. The coupling portion 331 of the injecting member 300 is a screw thread formed on the inner circumferential surface of the outer tube the double tube. Thus, there is provided a structure in which the outer tube of the cylinder 110 is inserted between the inner and outer tubes of the body portion 310 so that the screw threads are screwed with each other.

Therefore, according to the syringe for auto-regeneration of dermis having the aforementioned structure, by using the injecting member of the present invention formed separately by being coupled to the conventional liquid syringe circulated on the market, it is possible to differently manufacture the materials of the relatively expensive liquid syringe and the injecting member, the costs are reduced. Further, the liquid syringe and the injecting member are easily molded, and there is an advantage that is capable of repeatedly reusing the injecting member, unlike a liquid syringe that cannot be reused.

By limiting the shape of the inner surface of the body portion to the inverted cone-shape, the volume of liquid discharged varies during movement of the same stroke, so that it is possible to control the amount of liquid that is more finely injected. It is possible to inject the exact amount of liquid into the dermis with minimal residual gas.

Further, the dead space between the bottom of the cylinder and the check valve is suppressed to a minimum by limiting the internal diameter of the injecting member and the needle position, thereby preventing the discharge of liquid during the initial pressurization of the piston such that only the gas can be injected to the dermis. As a result, it is possible to completely perform injection in the order of gas-liquid-gas to the inside of the dermis. Further, by reducing the dead space, the liquid remaining in the cylinder can be fully used in the final step of finally using all the liquid, and the residual liquid can be easily recovered only by a simply operation when the liquid remains. Accordingly, there are advantages capable of efficiently using the relatively expensive liquid and preventing a cushioning effect.

The present invention has been described and illustrated with reference to specific embodiments, are provided by the following claims, within the scope not departing from the technical idea of the present invention, the present invention is variously improved and that may be changed is obvious to those skilled in the art.

While the present invention has been described and illustrated with reference to specific embodiments, it is obvious to those skilled in the art that the present invention can be variously improved and changed within the scope that does not depart from the technical idea of the present invention provided by the following claims.

The invention claimed is:

1. A syringe mechanism for auto-regeneration of dermis, comprising:
    a liquid syringe in which a liquid is filled inside a cylinder, a piston is inserted into a top of the cylinder, a discharge portion is formed at a bottom portion of the cylinder, and screw threads are formed around the discharge portion; and
    an injecting member in which a cylindrical body portion is provided, an inlet portion is formed to be inserted and coupled with the discharge portion at the top of the body portion, a coupling portion is formed to be coupled with the screw threads around the inlet portion, the screw threads and the coupling portion are rotated and fitted so as to be fastened to the liquid syringe so that liquid is injected into the top portion of the cylindrical body portion via the liquid syringe, an inlet check valve is provided at one side of the cylindrical body portion so that gas is injected into the cylindrical body portion via the inlet check valve, and a needle is coupled to the bottom of the cylindrical body portion so that gas or liquid from the cylindrical body portion is discharged to outside through the needle,
    wherein the cylindrical body portion is filled with the gas injected via the inlet check valve when the piston is pulled, and the gas and the liquid in the cylindrical body portion are discharged alternately to outside through the needle when the piston is pressed.

2. The syringe mechanism for auto-regeneration of dermis of claim 1, wherein an inner diameter of the body portion is 2 to 7 mm.

3. The syringe mechanism for auto-regeneration of dermis of claim 1, wherein an inner surface of the body portion has an inner diameter that becomes increasingly narrower as it goes toward the lower side.

4. The syringe mechanism for auto-regeneration of dermis of claim 3, wherein the inner surface of the body portion has an inverted cone-shape.

5. The syringe mechanism for auto-regeneration of dermis of claim 1, wherein a top corner of the inner side surface of the body portion has a round shape.

6. The syringe mechanism for auto-regeneration of dermis of claim 1, wherein a bottom edge of the inner side surface of the body portion has a round shape.

7. The syringe mechanism for auto-regeneration of dermis of claim 1, wherein the top of the needle is located between a point which is 2 mm below the bottom of a portion in which the inlet check valve is injected into the injecting member and a point which is 5 mm above the top of the inlet check valve.

8. The syringe mechanism for auto-regeneration of dermis of claim 1, further comprising:
a gas supply portion connected to the inlet check valve.

9. The syringe mechanism for auto-regeneration of dermis of claim 1, wherein a double tube which opens downward is formed on the lower surface of the cylinder, the inner tube of the double tube communicates with the cylinder to constitute the discharge portion, a screw thread is formed on an inner circumferential surface of an outer tube of the double tube, and a coupling portion of the injecting member has a flange shape formed along the periphery of the inlet portion, is inserted between the inner tube and the outer tube of the double tube and is coupled to the screw thread.

10. The syringe mechanism for auto-regeneration of dermis of claim 9, wherein the discharge portion is inserted into the inner diameter of the inlet portion in accordance with the screw coupling between the coupling portion and the screw thread.

11. The syringe mechanism for auto-regeneration of dermis of claim 10, wherein the discharge portion has a cone-shape having an outer diameter that becomes narrower as it goes downward, and the discharge portion is sealed in close contact with the inlet portion in a state of being inserted into the inlet portion.

12. The syringe mechanism for auto-regeneration of dermis of claim 9, wherein the inlet portion is an open hole formed at the top of the body portion of the injecting member, and the coupling portion has a flange shape formed along the periphery of the body portion of the point in which the open hole is formed.

13. The syringe mechanism for auto-regeneration of dermis of claim 1, wherein the discharge portion which communicates with the cylinder and opens downward is formed on the lower surface of the cylinder, a screw thread is formed on the outer circumferential surface of the discharge portion, the coupling portion of the injecting member is the screw thread formed along the inner circumferential surface of the inlet portion, and the discharge portion is inserted and screwed into the inlet portion.

14. The syringe mechanism for auto-regeneration of dermis of claim 1, wherein a double tube which opens downward is formed on the lower surface of the cylinder, the inner tube of the double tube communicates with the cylinder to constitute the discharge portion, the outer tube of the double tube has a screw thread formed on its outer circumferential surface, a double tube that opens upward is formed on the upper surface of the body portion, the inner tube of the double tube communicates with the body portion to constitute the inlet portion, the coupling portion of the injecting member is the screw thread formed on the inner circumferential surface of the outer tube, and the outer tube of the cylinder is inserted between the inner and outer tubes of the body portion such that the screw threads are coupled to each other.

\* \* \* \* \*